(12) United States Patent
Sato et al.

(10) Patent No.: US 10,595,811 B2
(45) Date of Patent: Mar. 24, 2020

(54) X-RAY COMPUTED TOMOGRAPHY APPARATUS

(71) Applicant: Toshiba Medical Systems Corporation, Otawara-shi (JP)

(72) Inventors: Asako Sato, Nasushiobara (JP); Yohei Matsuzawa, Nasushiobara (JP); Keisuke Oishi, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 245 days.

(21) Appl. No.: 15/855,006

(22) Filed: Dec. 27, 2017

(65) Prior Publication Data

US 2018/0177479 A1    Jun. 28, 2018

(30) Foreign Application Priority Data

Dec. 27, 2016  (JP) ................................ 2016-253014

(51) Int. Cl.
| | |
|---|---|
| *A61B 6/00* | (2006.01) |
| *A61B 6/03* | (2006.01) |
| *A61B 6/04* | (2006.01) |

(52) U.S. Cl.
CPC ............... *A61B 6/54* (2013.01); *A61B 6/032* (2013.01); *A61B 6/0407* (2013.01); *A61B 6/4447* (2013.01); *A61B 6/461* (2013.01); *A61B 6/5205* (2013.01)

(58) Field of Classification Search
CPC ......... A61B 6/54; A61B 6/032; A61B 6/0407; A61B 6/4447; A61B 6/461; A61B 6/5205
See application file for complete search history.

(56) References Cited

U.S. PATENT DOCUMENTS

| | | | | |
|---|---|---|---|---|
| 6,580,777 B1* | 6/2003 | Ueki | ..................... | A61B 6/032 378/15 |
| 2006/0104422 A1* | 5/2006 | Iisaku | ..................... | A61B 6/04 378/209 |

FOREIGN PATENT DOCUMENTS

| | | |
|---|---|---|
| JP | 2006-141577 | 6/2006 |
| JP | 2013-123595 | 6/2013 |
| JP | 2017-209160 A | 11/2017 |

* cited by examiner

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray computed tomography apparatus includes a gantry main body, a base, a first support frame, a second support frame and gantry control circuitry. The gantry control circuitry controls a tilt of the gantry main body, a movement of the table top by the first support frame, and a movement of the first support frame by the second support frame. The gantry control circuitry executes switching between a first tilt mode in which the gantry main body is tiltable in a first angle range and a second tilt mode in which the gantry main body is tiltable in a second angle range in which a tilt angle is greater than in the first angle range.

20 Claims, 10 Drawing Sheets

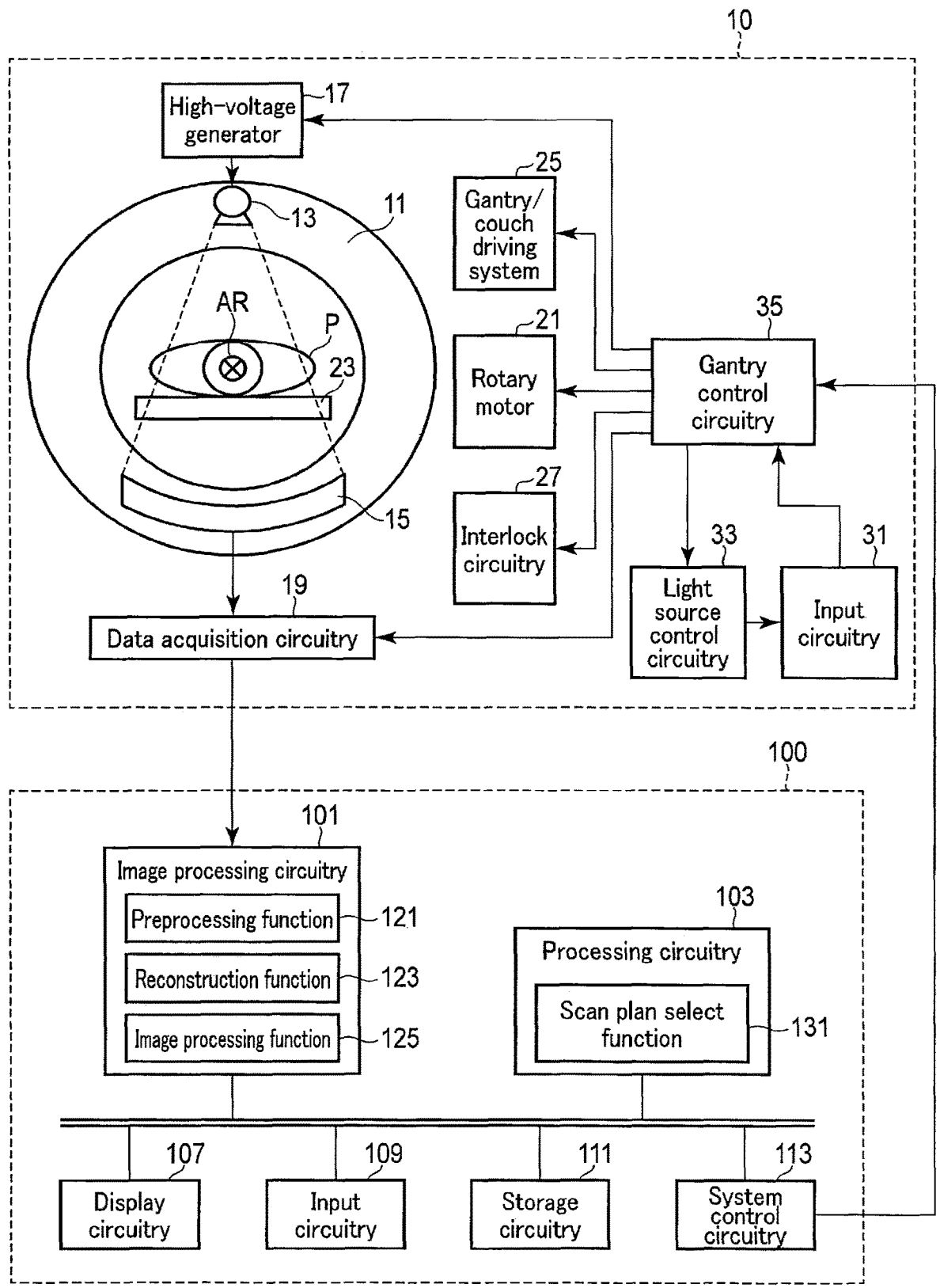
F I G. 1

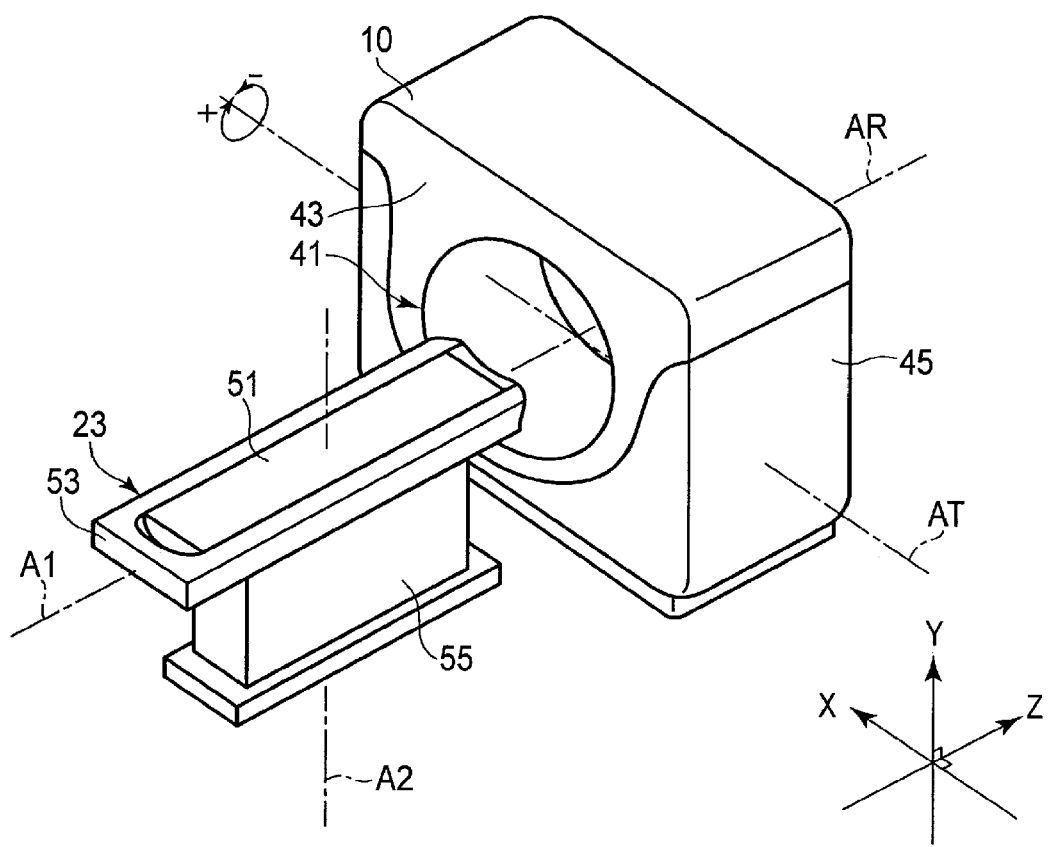
F I G. 2

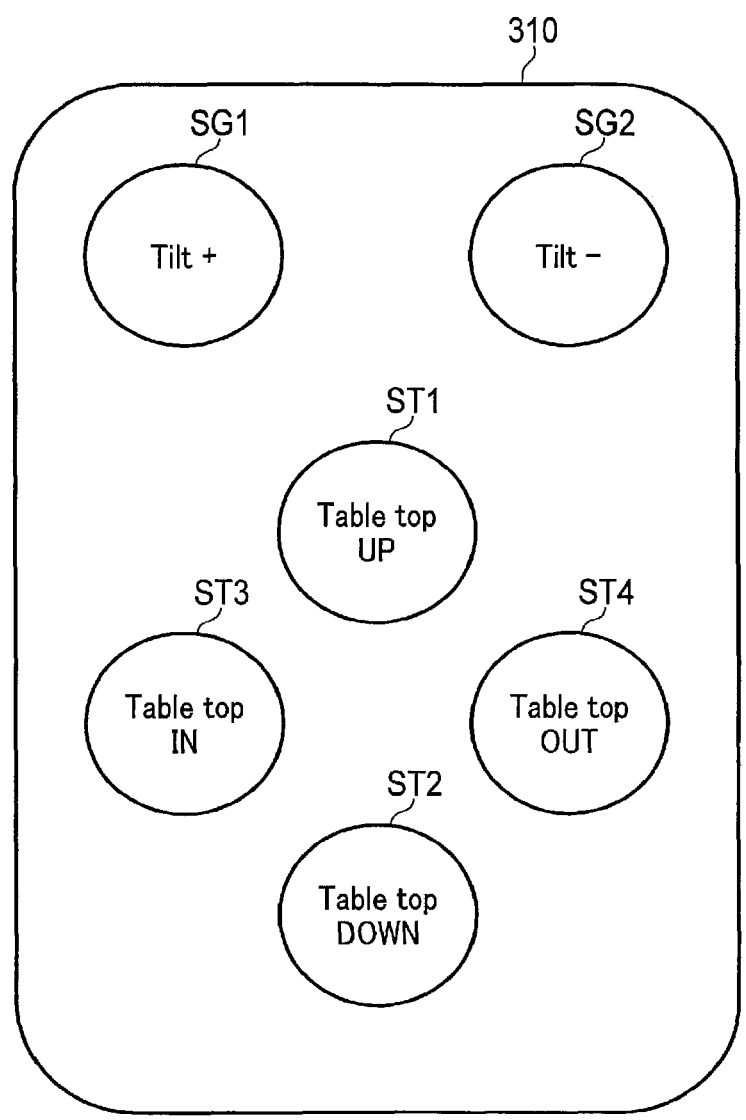
F I G. 3

X-RAY COMPUTED TOMOGRAPHY APPARATUS

CROSS-REFERENCE TO RELATED APPLICATIONS

This application is based upon and claims the benefit of priority from the prior Japanese Patent Application No. 2016-253014, filed Dec. 27, 2016, the entire contents of which are incorporated herein by reference.

FIELD

Embodiments described herein relate generally to an X-ray computed tomography apparatus.

BACKGROUND

In order to acquire a high-definition CT image, it is conceivable to reduce the bending of a table top of a bed. As one method for reducing the bending of the table top, there is known a method in which a frame that slidably supports the table top is moved as close as possible to a gantry. However, according to this method, since a clearance between the gantry and the frame decreases, the operable range of tilt angles is restricted. Although an interference can be avoided by restricting the tilt angle, the position of the frame, etc., it is not possible to exhibit to the maximum the capability of an X-ray computed tomography apparatus including this bed.

BRIEF DESCRIPTION OF THE DRAWINGS

FIG. 1 is a view illustrating the configuration of an X-ray computed tomography apparatus according to an embodiment.

FIG. 2 is a view which schematically illustrates the external appearance of a gantry and a bed according to the embodiment.

FIG. 3 is a view illustrating an example of an operation panel provided in input circuitry in FIG. 1.

DETAILED DESCRIPTION

Figure 4:
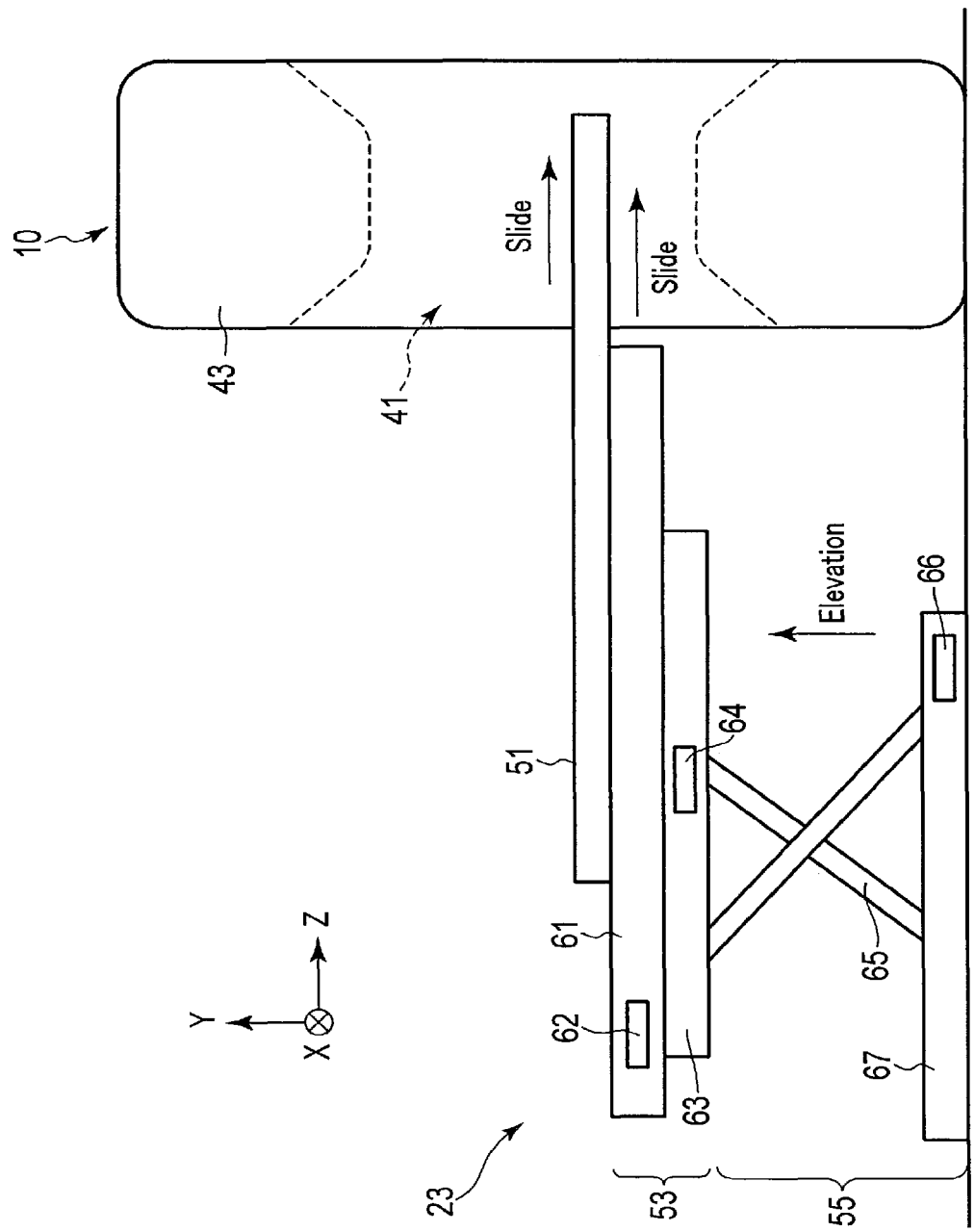
FIG. 4 is a view which schematically illustrates a lateral side of the bed according to the embodiment.

In general, according to one embodiment, an X-ray computed tomography apparatus includes a gantry main body, a base, a first support frame, a second support frame and gantry control circuitry. The gantry main body is equipped with an X-ray tube and an X-ray detector. The base tiltably supports the gantry main body. The first support frame supports a table top, on which a subject is placed, such that the table top is movable in a longitudinal direction. The second support frame supports the first support frame such that the first support frame is movable in the longitudinal direction. The gantry control circuitry controls a tilt of the gantry main body, a movement of the table top by the first support frame, and a movement of the first support frame by the second support frame. The gantry control circuitry executes switching between a first tilt mode in which the gantry main body is tiltable in a first angle range and a second tilt mode in which the gantry main body is tiltable in a second angle range in which a tilt angle is greater than in the first angle range.

Hereinafter, an X-ray computed tomography apparatus according to the embodiment will be described with reference to the accompanying drawings.

FIG. 1 is a view illustrating the configuration of the X-ray computed tomography apparatus according to the embodiment. As illustrated in FIG. 1, the X-ray computed tomography apparatus according to the embodiment includes a gantry 10 and a console 100. For example, the gantry 10 is installed in a CT examination room, and the console 100 is installed in a control room which neighbors the CT examination room. The gantry 10 and console 100 are communicably connected. The gantry 10 is equipped with a scan mechanism for performing X-ray CT scan of a subject P. The console 100 is a computer which controls the gantry 10.

As illustrated in FIG. 1, the gantry 10 includes a substantially cylindrical rotary frame 11 in which a bore is formed. As illustrated in FIG. 1, an X-ray tube 13 and an X-ray detector 15, which are disposed to face each other with the bore interposed, are attached to the rotary frame 11. The rotary frame 11 is a metallic frame which is formed of a metal, such as aluminum, in an annular shape.

The X-ray tube 13 is connected to a high-voltage generator 17. The high-voltage generator 17 is attached to, for example, the rotary frame 11. In accordance with the control by gantry control circuitry 35, the high-voltage generator 17 generates a high voltage which is applied to the X-ray tube 13, and supplies a filament heating current to the X-ray tube 13. The high-voltage generator 17 and X-ray tube 13 are connected via a high-voltage cable (not shown). A high voltage, which is generated by the high-voltage generator 17, is applied to the X-ray tube 13 via the high-voltage cable. In addition, the filament heating current, which is generated by the high-voltage generator 17, is applied to the X-ray tube 13 via the high-voltage cable.

The rotary frame 11 receives a driving force from a rotary motor 21, and rotates at a fixed angular velocity about a center axis AR. A discretionally chosen motor, such as a direct drive motor or a servo motor, is used as the rotary motor 21. For example, the rotary motor 21 is accommodated in the gantry 10. The rotary motor 21 receives a driving signal from the gantry control circuitry 35 and generates a driving force for rotating the rotary frame 11.

A table top, which is supported on a bed 23, is inserted in the bore of the rotary frame 11. The subject P is placed on the table top. The bed 23 is, for example, of a two-stage slide type. The bed 23 receives a driving force from a gantry/bed driving system 25 and freely moves the table top. The table top is positioned such that an imaging region of the placed subject P is included in an FOV (field of view).

FIG. 2 is a view which schematically illustrates the external appearance of the gantry 10 and bed 32. As illustrated in FIG. 2, the gantry 10 includes a gantry main body 43 in which a substantially cylindrical bore 41 is formed. The rotary frame 11, in the X-ray tube 13 and X-ray detector 15 are disposed with the bore 41 interposed, is accommodated in the gantry main body 43. The gantry main body 43 is supported on a base 45 installed on the floor surface, such that the gantry main body 43 is tiltable about a tilt axis AT. The tilt axis AT horizontally intersects at right angles with a rotational axis AR. Here, a direction in which a lower portion of the gantry main body 43 approaches the bed 23 is referred to as "+tilt direction", and a direction in which the lower portion of the gantry main body 43 moves away from the bed 23 is referred to as "−tilt direction".

As illustrated in FIG. 2, the bed 23 is disposed in front of the gantry 10. The bed 23 is equipped with a table top 51, an upper frame 61 and a support base 55. The table top 51 is disposed such that a longitudinal axis A1 of the table top 51 is parallel to the center axis AR of the bore 41. The upper frame 61 supports the table top 51 such that the table top 51 is slidable along the longitudinal axis A1 of the table top 51. The support base 55 supports the upper frame 61 such that the upper frame 61 can slide along an axis parallel to the longitudinal axis A1 and can elevate along a vertical axis A2 which vertically intersects at right angles with the longitudinal axis A1. The support base 55 has a cantilever support structure. Specifically, the support base 51 supports the table top 51 and upper frame 61 from only one side with respect to the direction of the longitudinal axis A1. Here, an axis parallel to the longitudinal axis A1 is defined as a Z axis, and an axis parallel to the vertical axis A2 is defined as a Y axis. An axis perpendicular to the Z axis and Y axis is defined as an X axis. An XYZ coordinate system constitutes an orthogonal coordinate system. Hereinafter, a direction parallel to the longitudinal axis A1 of the table top 51 is referred to as a longitudinal direction or a Z direction, and a direction parallel to the vertical axis A2 is referred to as a vertical direction or a Y direction. In addition, a direction in which the bed 23 approaches the gantry 10 is referred to as "+Z direction", and a direction in which the bed 23 moves away from the gantry 10 is referred to as "−Z direction". A direction in which the bed 23 rises is referred to as "+Y direction", and a direction in which the bed 23 lowers is referred to as "−Y direction".

As illustrated in FIG. 1, the gantry/bed driving system 25 includes a driving device relating to the movement of the gantry 10 such as a tilt of the gantry 10, and a driving device relating to the movement of the bed 23. The gantry/bed driving system 25 receives a driving signal from the gantry control circuitry 35 and generates a driving force. The details of the gantry/bed driving system 25 will be described later.

Interlock circuitry 27 switches a mode (hereinafter referred to as "interlock mode") relating to the movable ranges of the gantry 10 and bed 23 between a bending reduction mode and a tilt priority mode. The bending reduction mode and tilt priority mode will be described later.

The X-ray detector 15 detects X-rays which are generated from the X-ray tube 13. Specifically, the X-ray detector 15 includes a plurality of detection elements which are arranged on a two-dimensional curved surface. Each of the detection elements includes a scintillator and a photoelectric converter element. The scintillator is a material which converts X-rays to fluorescence. The scintillator converts incident X-rays to fluorescence photons, the number of which corresponds to the intensity of the incident X-rays. The photoelectric converter element is a circuitry element which amplifies the fluorescence and converts the fluorescence to an electric signal. As the photoelectric converter element, for example, a photomultiplier or a photodiode is used. Besides, the detection element may be of an indirect conversion type which executes detection after converting X-rays to light as described above, or may be of a direct conversion type which directly converts X-rays to an electric signal. As the detection element of the direct conversion type, for example, use can be made of a type including a semiconductor diode configured such that electrodes are attached to both ends of a semiconductor.

Data acquisition circuitry 19 is connected to the X-ray detector 15. The data acquisition circuitry 19 acquires, with respect to each view, data (hereinafter referred to as "raw data"), which corresponds to the intensity of X-rays detected by the X-ray detector 15, from the X-ray detector 15. Specifically, the data acquisition circuitry 19 includes, for example, integration circuitry (not shown) and an A/D converter (not shown) in association with each of the detection elements. The integration circuitry integrates the electric signal from the detection element with respect to each view. The A/D converter converts the integrated electric signal from an analog signal to a digital signal (raw data). Thereby, the raw data of each view is acquired. The raw data is a set of digital values indicative of the intensity of X-rays identified by a channel number and a row number of the detection element of the generation source, and a view number indicative of the acquired view. The raw data is supplied to the console 100, for example, via a non-contact data transmission device (not shown) which is accommodated in the gantry 10. Besides, other circuitry elements such as a preamplifier and an IV converter may be included in the data acquisition circuitry 19. The data acquisition circuitry 19 includes a semiconductor integrated circuit such as an ASIC (Application Specific Integrated Circuit), and the above-described circuitry elements such as the integration circuitry and A/D converter are included in the semiconductor integrated circuit.

Input circuitry 31 includes an operation panel which includes a plurality of switches for operating the gantry 10 and bed 23. The operation panel is provided on the front side of the gantry main body 43. The input circuitry 31 supplies an output signal from a depressed switch to the gantry control circuitry 35.

FIG. 3 is a view illustrating an example of the operation panel 310. As illustrated in FIG. 3, the operation panel 310 includes, for example, bed switches ST relating to the operation of the bed 23, and gantry switches SG relating to the operation of the gantry main body 43. As the bed switches ST, for example, a table top UP switch ST1, a table top DOWN switch ST2, a table top IN switch ST3 and a table top OUT switch ST4 are provided. As the gantry switches SG, for example, a tilt+ switch SG1 and a tilt− switch SG2 are provided.

The tilt+ switch SG1 is a switch to which a function for tilting the gantry main body 43 in a +direction about the axis AT is allocated. When the tilt+ switch SG1 was depressed, the gantry control circuitry 35 supplies a control signal instructing a tilt in the +direction to the gantry/bed driving system 25. Upon receiving this control signal, the gantry/bed driving system 25 tilts the gantry main body 43 in the +direction. The tilt− switch SG2 is a switch to which a function for tilting the gantry main body 43 in a −direction about the axis AT is allocated. When the tilt− switch SG2 was depressed, the gantry control circuitry 35 supplies a control signal instructing a tilt in the −direction to the gantry/bed driving system 25. Upon receiving this control signal, the gantry/bed driving system 25 tilts the gantry main body 43 in the −direction.

The table top UP switch ST1 is a switch to which a function of moving the table top 51 in the +Y direction, that is, raising the table top 51, is allocated. When the table top UP switch ST1 was depressed, the gantry control circuitry 35 supplies a control signal instructing the raising to the gantry/bed driving system 25. Upon receiving this control signal, the gantry/bed driving system 25 raises the table top 51. The table top DOWN switch ST2 is a switch to which a function of moving the table top 51 downward (−Y direction), that is, lowering the table top 51, is allocated. When the table top DOWN switch ST2 was depressed, the gantry control circuitry 35 supplies a control signal instructing the lowering to the gantry/bed driving system 25. Upon receiving this control signal, the gantry/bed driving system 25 lowers the table top 51. The table top IN switch ST3 is a switch to which a function of moving the table top 51 closer to the gantry main body 43 in the +Z direction, that is, advancing the table top 51, is allocated. When the table top IN switch ST3 was depressed, the gantry control circuitry 35 supplies a control signal instructing the advancing to the gantry/bed driving system 25. Upon receiving this control signal, the gantry/bed driving system 25 advances the table top 51. The table top OUT switch ST4 is a switch to which a function of moving the table top 51 away from the gantry main body 43 in the −Z direction, that is, retreating the table top 51, is allocated. When the table top OUT switch ST4 was depressed, the gantry control circuitry 35 supplies a control signal instructing the retreating to the gantry/bed driving system 25. Upon receiving this control signal, the gantry/bed driving system 25 retreats the table top 51.

The switches SG1, SG2, ST1, ST2, ST3 and ST4 are provided with light sources. Each light source is turned on, flickered, or turned off in accordance with a driving signal from light source control circuitry 33. Incidentally, the above-described operation panel 310 is merely an example. The switches mounted in the operation panel 310 are not restricted to those described, and other kinds of switches may be mounted.

The light source control circuitry 33, as illustrated in FIG. 1, supplies driving signals to the light sources which are provided in the switches included in the input circuitry 31. Examples of the driving signals are a turn-on signal which instructs turn-on, a flicker signal which instructs flickering, and a turn-off signal which instructs turn-off. The light source control circuitry 33 selectively supplies the turn-on signal, flicker signal and turn-off signal to the light sources in accordance with an instruction from the gantry control circuitry 35.

The gantry control circuitry 35 synchronously controls the high-voltage generator 17, data acquisition circuitry 19, rotary motor 21 and gantry/bed driving system 25 in order to execute X-ray CT scan according to a scan plan selected by the console 100. In addition, the gantry control circuitry 35 controls the gantry/bed driving system 25 and moves the gantry 10 and bed 23 interlockingly in order to realize positioning between the gantry 10 and bed 23 with less bending of the table top. The gantry control circuitry 35 includes, as hardware resources, processing devices (processors) such as a CPU (Central Processing Unit) and an MPU (Micro Processing Unit), and storage devices (memories) such as a ROM (Read Only Memory) and a RAM (Random Access Memory). In addition, the gantry control circuitry 35 may be realized by an ASIC, an FPGA (Field Programmable Gate Array), a CPLD (Complex Programmable Logic Device) or an SPLD (Simple Programmable Logic Device). The details of the gantry control circuitry 35 will be described later.

As illustrated in FIG. 1, the console 100 includes image processing circuitry 101, processing circuitry 103, display circuitry 107, input circuitry 109, storage circuitry 111 and system control circuitry 113. Data communication between the image processing circuitry 101, processing circuitry 103, display circuitry 107, input circuitry 109, storage circuitry 111 and system control circuitry 113 is executed via a bus.

The image processing circuitry 101 includes as hardware resources a processor such as a GPU (Graphics Processing Unit), and storage devices such as a ROM and a RAM. The image processing circuitry 101 includes a preprocessing function 121, a reconstruction function 123 and an image processing function 125. In the preprocessing function 121, the image processing circuitry 101 executes preprocessing, such as logarithmic conversion, on the raw data transmitted from the gantry 10. The raw data after the preprocessing is also called "projection data". In the reconstruction function 123, the image processing circuitry 101 generates, based on the preprocessed raw data, a CT image which represents a spatial distribution of CT values relating to the subject P. As an image reconstruction algorithm, use may be made of a conventional image reconstruction algorithm such as an FBP (filtered back projection) method or an iterative reconstruction method. In the image processing function 125, the image processing circuitry 101 applies various image processes to the CT image. For example, the image processing circuitry 101 generates a display image by applying to the CT image a three-dimensional image process such as volume rendering, surface volume rendering, an image value projection process, an MPR (Multi-Planar Reconstruction) process, or a CPR (Curved MPR) process.

The processing circuitry 103 includes as hardware resources a processor such as a CPU, and storage devices such as a ROM and a RAM. The processing circuitry 103 includes, for example, a scan plan select function 131. In the scan plan select function 131, the processing circuitry 103 selects a scan plan relating to an X-ray CT scan using the subject P as a target, in accordance with an instruction via the input circuitry 109 by the user, or automatically.

The display circuitry 107 displays various data such as two-dimensional CT images and display images. Specifically, the display circuitry 107 includes a display interface and a display device. The display interface converts data representing a display target to a video signal. The video signal is supplied to the display device. The display device displays the video signal representing the display target. As the display device, for example, use can be made of, as needed, a CRT display, a liquid crystal display, an organic EL display, an LED display, a plasma display, or some other discretionarily chosen display known in the technical field.

The input circuitry 109 inputs various instructions from the user. Specifically, the input circuitry 109 includes an input device and an input interface. The input device accepts various instructions from the user. As the input device, a keyboard, a mouse and various switches can be used. The input interface supplies an output signal from the input device to the system control circuitry 113 via the bus.

The storage circuitry 111 is a storage device which stores various kinds of information, such as an HDD, an SSD, and an integrated circuit storage device. Besides, the storage circuitry 111 may be a drive such as a CD-ROM drive, a DVD drive or a flash memory, which reads/writes various kinds of information from/to a portable storage medium. For example, the storage circuitry 111 stores data of CT images and display images. In addition, the storage circuitry 111 stores control programs, etc. relating to the X-ray CT scan according to the embodiment.

The system control circuitry 113 includes, as hardware resources, processors such as a CPU and an MPU, and memories such as a ROM and a RAM. Besides, the system control circuitry 113 may be realized by an ASIC, an FPGA, a CPLD, or an SPLD. The system control circuitry 113 functions as a central unit of the X-ray computed tomography apparatus according to the embodiment. Specifically, the system control circuitry 113 reads out a control program stored in the storage circuitry 111, develops the control program on the memory, and controls the respective components of the X-ray computed tomography apparatus according to the developed control program.

Hereinafter, the operation of the X-ray computed tomography apparatus according to the present embodiment will be described in detail.

To begin with, the configuration of the bed 23 will be described with reference to FIG. 4. FIG. 4 is a view which schematically illustrates a lateral side of the bed 23 according to the embodiment. In FIG. 4, the housing of the bed 23 is not illustrated. As illustrated in FIG. 4, the bed 23 includes the table top 51, a support frame 53 and the support base 55. The table top 51 is a flexible plate-like structure. The table top 51 is formed of a material with a relatively high X-ray transmittance, such as urethane foam or carbon. The support frame 53 supports the table top 51. The support frame 53 includes the upper frame 61 and a lower frame 63. The lower frame 63 is fixed to the support base 55. The lower frame 63 supports the upper frame 61 slidably in the Z direction.

As illustrated in FIG. 4, the table top 51 is supported by the upper frame 61 such that the table top 51 is slidable in the Z direction. The upper frame 61 has any configuration if the upper frame 61 can slide the table top 51. For example, the upper frame 61 includes a robust frame having a frame shape (not shown) which supports the table top 51, and a guide rail (not shown) which is provided in the robust frame and guides the table top 51 in the Z direction. The upper frame 61 is provided with a table top driving control device 62 which generates a driving force for sliding the table top 51 in the Z direction. The table top driving control device 62 is realized by a conventional motor such as a servo motor. The table top driving control device 62 is operated by the control of the gantry control circuitry 35.

As illustrated in FIG. 4, the lower frame 63 supports the upper frame 61 such that the upper frame 61 can slide in the Z direction. The lower frame 63 may have any configuration if the lower frame 63 can slide the upper frame 61. For example, the lower frame 63 is realized by a ball screw. The lower frame 63 is provided with a frame driving control device 64 which generates a driving force for sliding the upper frame 61 in the Z direction. The frame driving control device 64 is realized by a conventional motor such as a servo motor. The frame driving control device 64 is operated by the control of the gantry control circuitry 35.

As illustrated in FIG. 4, the support base 55 is installed on the floor surface. The support base 55 includes a support structure which can raise or lower the lower frame 63 in the Y direction, while moving the lower frame 63 toward or away from the gantry 10. For example, the support base 55 includes an X link 65 and a base 67. The X link 65 is connected to the lower frame 63 and base 67. The base 67 is provided with an elevation driving control device 66 which generates a driving force for raising and lowering the lower frame 63 in the Y direction by the X link 65. The elevation driving control device 66 is realized by a conventional motor such as a servo motor. The elevation driving control device 66 is operated by the control of the gantry control circuitry 35.

Figure 5:
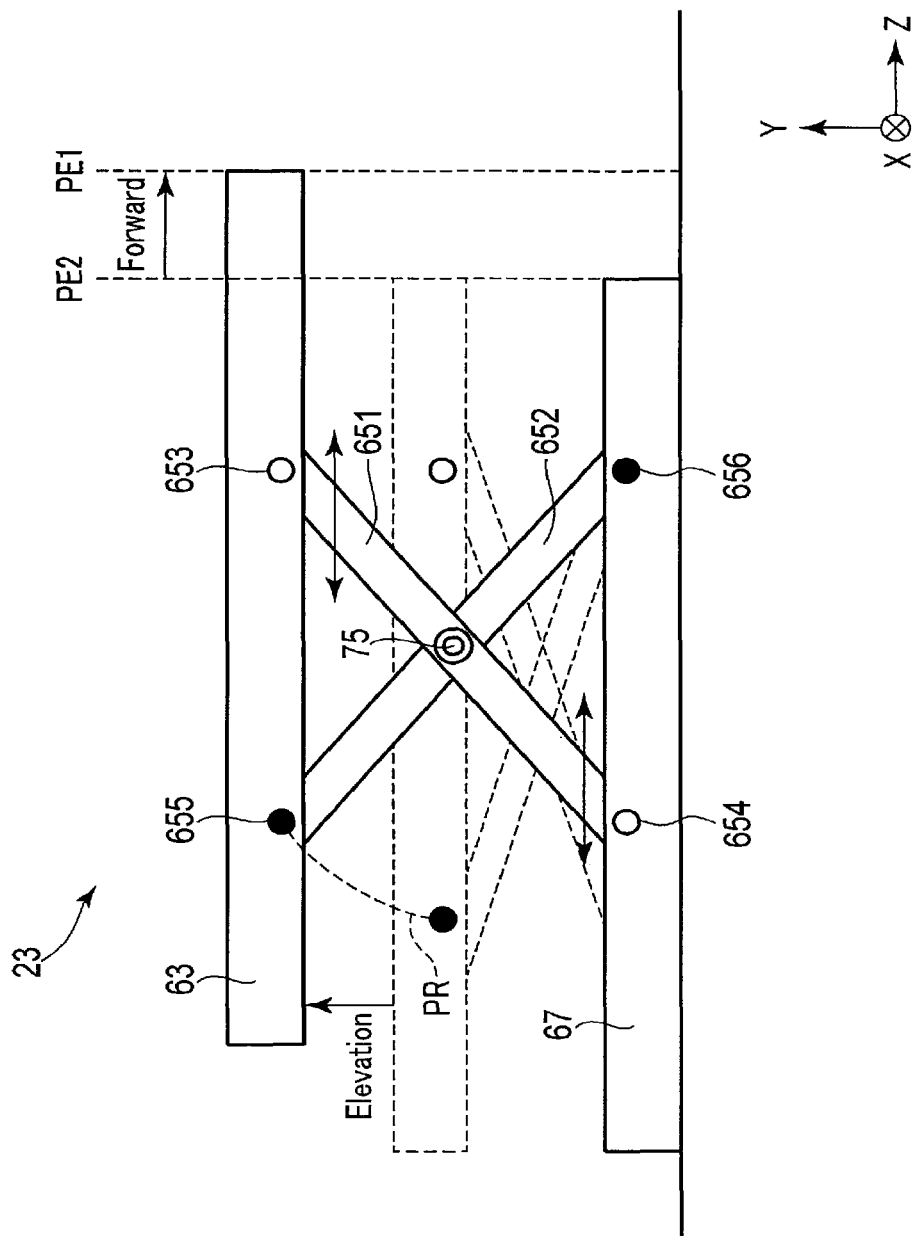
FIG. 5 is a view illustrating a forward movement of the bed according to the embodiment.

Next, referring to FIG. 5, a description will be given of a forward movement of the two-stage slide-type bed 23 which is equipped with the X link 65. FIG. 5 is a view illustrating the forward movement of the bed 23. In FIG. 5, the bed 23 positioned at a lower-limit height is indicated by a broken line, and the bed 23 after elevation is indicated by a solid line.

As illustrated in FIG. 5, the X link 65 includes a pair of a movable link 651 and a stationary link 652 which are pivotally supported in an X shape. The movable link 651 and stationary link 652 are provided to be rotatable about a fulcrum 75. The movable link 651 and stationary link 652 are formed of, for example, a pair of metal plates each having a plate shape and a substantially equal length. An end portion 656 of the stationary link 652 is fixed to the base 67. For example, this end portion is fixed to the base 67 by a fastening tool or the like. The other end portion 655 of the stationary link 652 is fixed to the lower frame 63. An end portion 654 of the movable link 651 is supported by the base 67 such that this end portion 654 is slidable in the Z direction. The other end portion 653 of the movable link 651 is supported by the lower frame 63 such that this end portion 653 is slidable in the Z direction.

When a driving shaft of the elevation driving control device 66 rotates in a forward direction, the movable link 651 moves in the +Z direction in interlock with this rotation, and the distance in the Z direction between the movable link 651 and stationary link 652 decreases. Thereby, the lower frame 63 is raised in the +Y direction. When the driving shaft of the elevation driving control device 66 rotates in a reverse direction, the movable link 651 moves in the −Z direction in interlock with this rotation, and the distance in the Z direction between the movable link 651 and stationary link 652 increases. Thereby, the lower frame 63 is lowered in the −Y direction.

As illustrated in FIG. 5, it is assumed that an end portion in the Z direction of the lower frame 63 at the lower-limit height, to be more specific, the end portion in the Z direction of the lower frame 63, is disposed at a position PE1 in the Z direction. As described above, the end portion 653 of the movable link 651 is provided on the lower frame 63 so as to be slidable in the Z direction, and the end portion 654 of the movable link 651 is provided on the base 67 so as to be slidable in the Z direction. The end portion 655 of the stationary link 652 is fixed to the lower frame 63, and the end portion 656 of the stationary link 652 is fixed to the base 67. Thus, by the movement of the movable link 651 in the +Z direction, the end portion 655 moves along an arc PR having as a radius a straight line connecting the end portion 655 and end portion 656, with the end portion 656 being set as a fulcrum. The position of the end portion 655 in the lower frame 63 and the position of the end portion 656 in the base 67 are unchanged before and after the movement. Accordingly, the end portion in the Z direction of the lower frame 63 moves forward in the +Z direction, that is, toward the gantry 10. For example, when the table top is raised to a target height, the end portion in the Z direction of the lower frame 63 moves forward to a position PE2 which is closer to the gantry 10 side than the position PE1 at the lower-limit height. In this manner, by the lower frame 63 moving forward to the gantry 10, the upper frame 61 can be moved as close as possible to the gantry main body 43.

As described above, the gantry 10 and bed 23 have two interlock modes, namely the bending reduction mode and tilt priority mode. The gantry control circuitry 35 according to the present embodiment automatically switches the interlock mode between the bending reduction mode and tilt priority mode in accordance with the position between the gantry main body 43 and upper frame 61. Specifically, the distance between the gantry main body 43 and upper frame 61 is determined based on the height of the upper frame 61 and the tilt angle of the gantry main body 43. Aside from this, for example, the distance between the gantry main body 43 and upper frame 61 may be determined based on the height of the upper frame 61 and a right-and-left movement position of the gantry main body 43.

Figure 6:
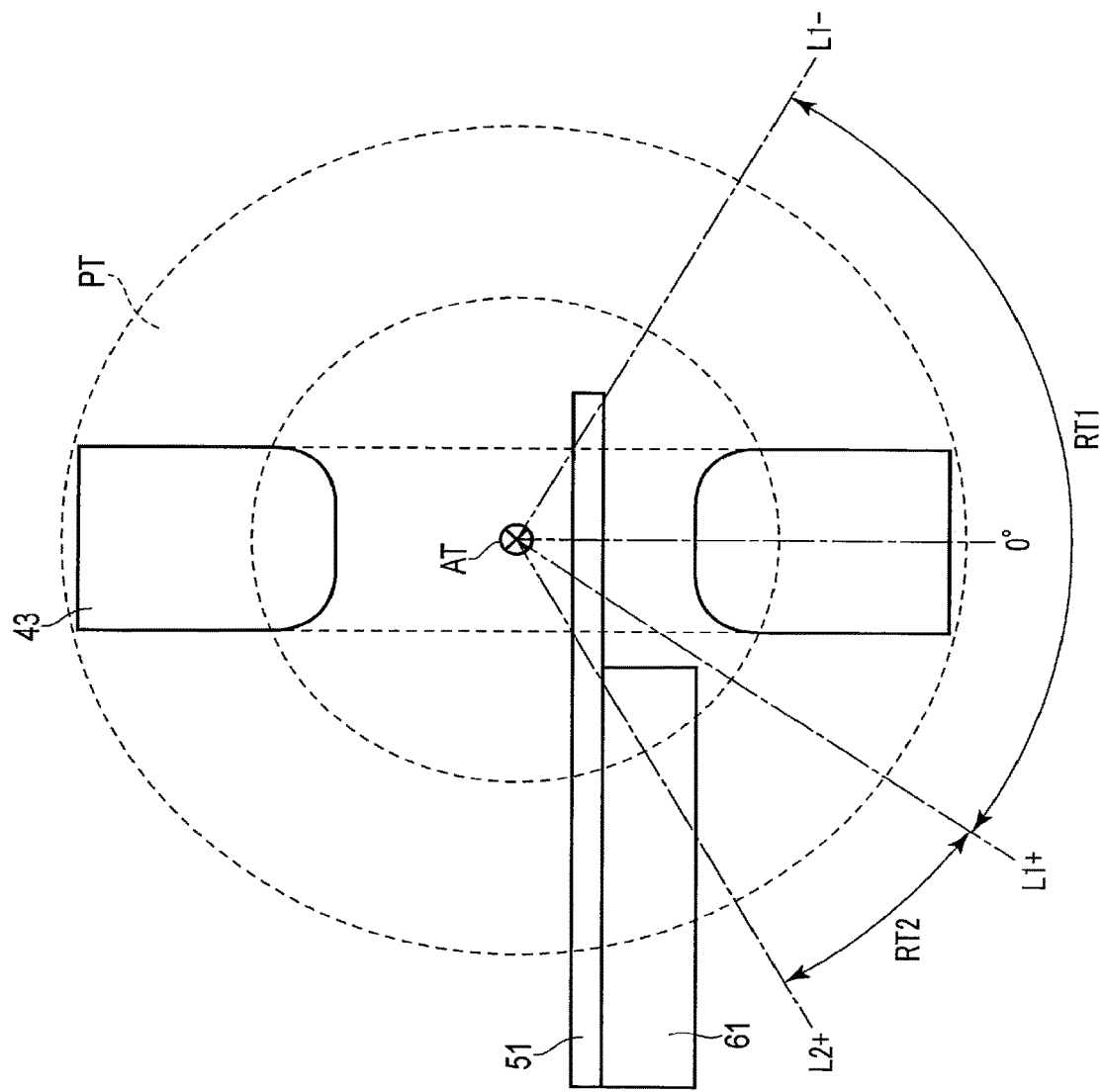
FIG. 6 is a view illustrating angle ranges of a bending reduction mode and a tilt priority mode, these angle ranges being superimposed on a schematic view illustrating a gantry main body and upper frame according to the embodiment, which are viewed from the lateral side.

FIG. 6 is a view illustrating angle ranges of the bending reduction mode and tilt priority mode, these angle ranges being superimposed on a schematic view illustrating the gantry main body 43 and upper frame 61 which are viewed from the lateral side. As illustrated in FIG. 6, the gantry main body 43 is supported by the base 45 (not shown) such that the gantry main body 43 can tilt about the tilt axis AT along a locus PT.

The bending reduction mode is an interlock mode in which the upper frame 61 is moved as close as possible to the gantry main body 43 in order to reduce the bending of the table top 51. The bending reduction mode is set when the tilt angle of the gantry main body 43 is in a predetermined angle range RT1 including the tilt angle of 0°. The angle range RT1 is defined as a range between a tilt angle L1+ in the tilt+ direction and a tilt angle L1− in the tilt− direction. In this embodiment, the tilt angle at a time when the gantry main body 43 is vertically positioned is defined as 0°. The tilt angle L1+ is a maximum tilt angle at which the gantry main body 43 and upper frame 61 can be made to approach each other to a proximity distance without physical interference. The proximity distance is a gantry-bed distance at a time when the upper frame 61 and gantry main body 43 have approached each other as close as possible, and the proximity distance can be discretionarily set by the user, etc. Specifically, the angle range RT1 is defined as an angle range in which the gantry main body 43 and upper frame 61 can approach each other to the proximity distance without physical interference. In the bending reduction mode, the upper frame 61 is positioned so as to approach as close as possible to the gantry main body 43 in order to reduce the bending of the table top 51. Concretely, the upper frame 61 and gantry main body 43 are positioned such that the gantry-bed distance agrees with the proximity distance.

The tilt priority mode is an interlock mode in which priority is placed on the tilt of the gantry main body 43 over the reduction of bending. The tilt priority mode is set when the tilt angle of the gantry main body 43 is in an angle range RT2 in which the tilt angle is greater than in the angle range RT1. The angle range RT2 is defined as a range between the tilt angle L1+ and a tilt angle L2+ which is greater than the tilt angle L1+. The tilt angle L2+ is defined as a maximum angle at which the gantry main body 43 can tilt without physical interference with the bed 23 when the upper frame 61 is moved backward to a maximum in the −Z direction. Because of structures of the bed 23 and gantry main body 43, the upper frame 61 cannot be made to approach the gantry main body 43 to the proximity range in the angle range RT2. Accordingly, when the gantry main body 43 is tilted at a tilt angle in the angle range RT2, the gantry main body 43 is tilted at a target tilt angle after the upper frame 61 is moved backward to a predetermined position (hereinafter referred to as "backward movement position") where there is no possibility that the upper frame 61 interferes with the gantry main body 43.

Besides, the angle range RT1 is the angle range in which the gantry main body 43 and upper frame 61 can approach each other at the proximity distance without physical interference. Thus, because of the structures of the gantry 10 and bed 23, the angle range RT1 varies in accordance with the height of the upper frame 61. Like the angle range RT1, the angle range RT2 varies in accordance with the height of the upper frame 61. The gantry control circuitry 35 stores a lookup table (hereinafter referred to as "angle range table") in which the angle range RT1 and angle range RT2 are associated with respect to each of the heights of the upper frame 61.

As described above, in the angle range RT1 of the bending reduction mode, the upper frame 61 is disposed at a position away from the gantry main body 43 by the proximity distance. In the angle range RT2 of the tilt priority mode, the upper frame 61 is disposed at the above-described backward movement position. Thus, the gantry control circuitry 35 according to this embodiment automatically switches the interlock mode by judging the Z-directional position of the upper frame 61, based on the height of the upper frame 61 and the tilt angle of the gantry main body 43. Thereby, the interlock mode can be switched without the user being aware of the position of the upper frame 61.

Figure 7:
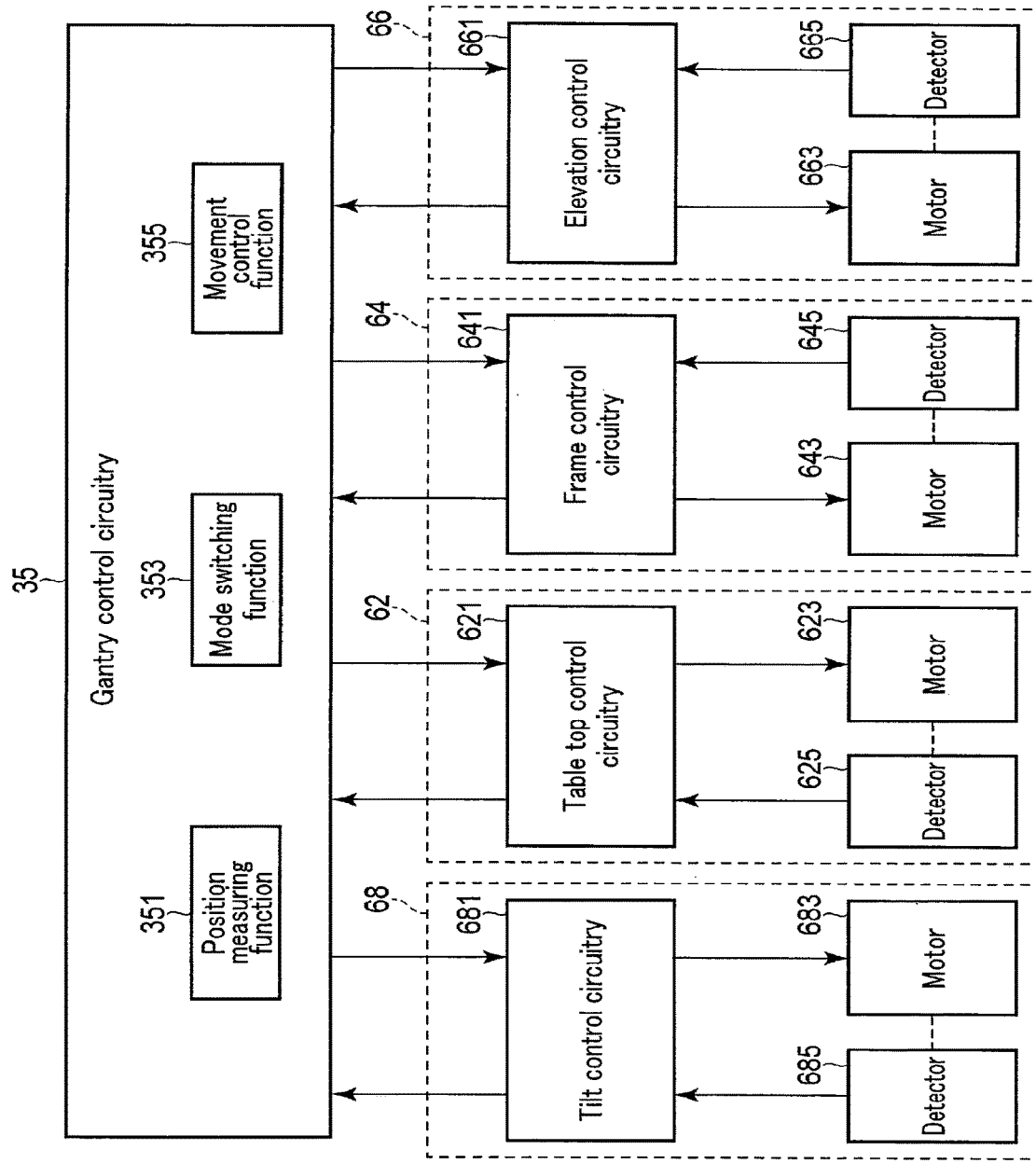
FIG. 7 is a view illustrating an example of the configuration of a gantry/bed driving system and gantry control circuitry according to the present embodiment.

FIG. 7 is a view illustrating an example of the configuration of the gantry/bed driving system 25 and gantry control circuitry 35 according to the present embodiment. As illustrated in FIG. 7, the gantry/bed driving system 25 includes a tilt driving control device 68, touch top driving control device 62, frame driving control device 64 and elevation driving control device 66.

The tilt driving control device 68 is provided in the gantry 10. The tilt driving control device 68 receives an operation instruction signal from the gantry control circuitry 35 and tilts the gantry 10. Specifically, the tilt driving control device 68 includes tilt control circuitry 681, a motor 683 and a detector 685. The tilt control circuitry 681 receives an operation instruction signal from the gantry control circuitry 35 and supplies electric power corresponding to this operation instruction signal to the motor 683. Specifically, the tilt control circuitry 681 is a servo amplifier which includes power supply circuitry which generates electric power that is supplied to the motor 683, and control circuitry which controls the power supply circuitry, based on a position signal from the detector 685. The motor 683 is driven by receiving electric power from the tilt control circuitry 681, and tilts the gantry 10. Specifically, the motor 683 is a motor which generates a driving force by the rotation of the driving shaft thereof. The detector 685 is a position detector which is provided on the driving shaft of the motor 683. The detector 685 is a rotary encoder which outputs a pulse signal (position signal) each time the driving shaft of the motor 683 rotates by a predetermined angle.

The table top driving control device 62 is provided, for example, in the upper frame 61. The table top driving control device 62 receives an operation instruction signal from the gantry control circuitry 35 and slides the table top 51. Specifically, the table top driving control device 62 includes table top control circuitry 621, a motor 623 and a detector 625. The table top control circuitry 621 receives an operation instruction signal from the gantry control circuitry 35 and supplies electric power corresponding to this operation instruction signal to the motor 623. Specifically, the table top control circuitry 621 is a servo amplifier which includes power supply circuitry which generates electric power that is supplied to the motor 623, and control circuitry which controls the power supply circuitry, based on a position signal from the detector 625. The motor 623 is driven by receiving electric power from the table top control circuitry 621, thereby operating the upper frame 61 to which the motor 623 is connected, and sliding the table top 51. Specifically, the motor 623 is a motor which generates a driving force by the rotation of the driving shaft thereof. The detector 625 is a position detector which is provided on the driving shaft of the motor 623. The detector 625 is a rotary encoder which outputs a pulse signal (position signal) each time the driving shaft of the motor 623 rotates by a predetermined angle.

The frame driving control device 64 is provided, for example, in the lower frame 63. The frame driving control device 64 receives an operation instruction signal from the gantry control circuitry 35 and slides the upper frame 61. Specifically, the frame driving control device 64 includes frame control circuitry 641, a motor 643 and a detector 645. The frame control circuitry 641 receives an operation instruction signal from the gantry control circuitry 35 and supplies electric power corresponding to this operation instruction signal to the motor 643. Specifically, the frame control circuitry 641 is a servo amplifier which includes power supply circuitry which generates electric power that is supplied to the motor 643, and control circuitry which controls the power supply circuitry, based on a position signal from the detector 645. The motor 643 is driven by receiving electric power from the frame control circuitry 641, thereby operating the lower frame 63 to which the motor 643 is connected, and sliding the upper frame 61. Specifically, the motor 643 is a motor which generates a driving force by the rotation of the driving shaft thereof. The detector 645 is a position detector which is provided on the driving shaft of the motor 643. The detector 645 is a rotary encoder which outputs a pulse signal (position signal) each time the driving shaft of the motor 643 rotates by a predetermined angle.

The elevation driving control device 66 is provided, for example, in the support base 55. The elevation driving control device 66 receives an operation instruction signal from the gantry control circuitry 35, operates the X link 65 and raises and lowers (vertically moves) the table top 51 and support frame 53. Specifically, the elevation driving control device 66 includes elevation control circuitry 661, a motor 663 and a detector 665. The elevation control circuitry 661 receives an operation instruction signal from the gantry control circuitry 35 and supplies electric power corresponding to this operation instruction signal to the motor 663. Specifically, the elevation control circuitry 661 is a servo amplifier which includes power supply circuitry which generates electric power that is supplied to the motor 663, and control circuitry which controls the power supply circuitry, based on a position signal from the detector 665. The motor 663 is driven by receiving electric power from the elevation control circuitry 661, thereby operating the X link 65 to which the motor 663 is connected, and raising and lowering the table top 51 and support frame 53. The detector 665 is a position detector which is provided on the driving shaft of the motor 663. The detector 665 is a rotary encoder which outputs a pulse signal (position signal) each time the driving shaft of the motor 663 rotates by a predetermined angle.

The gantry control circuitry 35 controls the gantry/bed driving system 25, based on a user instruction that is input via the input circuitry 31, or position signals from the detector 685, detector 625, detector 645 and detector 665. The gantry control circuitry 35 according to the present embodiment executes, concretely, a position measuring function 351, a mode switching function 353 and a movement control function 355.

In the position measuring function 351, the gantry control circuitry 35 measures the positions of the table top 51, upper frame 61 and gantry main body 43, based on position signals from the detector 685, detector 625, detector 645 and detector 665. Specifically, the gantry control circuitry 35 measures the tilt angle of the gantry main body 43, based on the position signal from the detector 685, measures the Z-directional position of the table top 51, based on the position signal from the detector 625, measures the Z-directional position of the upper frame 61, based on the position signal from the detector 645, and measures the height of the table top 51 and upper frame 61, based on the position signal from the detector 665.

In the mode switching function 353, the gantry control circuitry 35 sets the Z-directional position of the upper frame 61 in accordance with the height of the upper frame 61 and the tilt angle of the gantry main body 43, which were measured by the position measuring function 351. In accordance with the Z-directional position of the upper frame 61, the gantry control circuitry 35 switches the interlock mode by the interlock circuitry 27 between the bending reduction mode and tilt priority mode.

In the movement control function 355, the gantry control circuitry 35 individually or synchronously controls the touch top driving control device 62, frame driving control device 64 and elevation driving control device 66, and individually or synchronously moves the table top 51, support frame 53 and X link 65.

Figure 8:
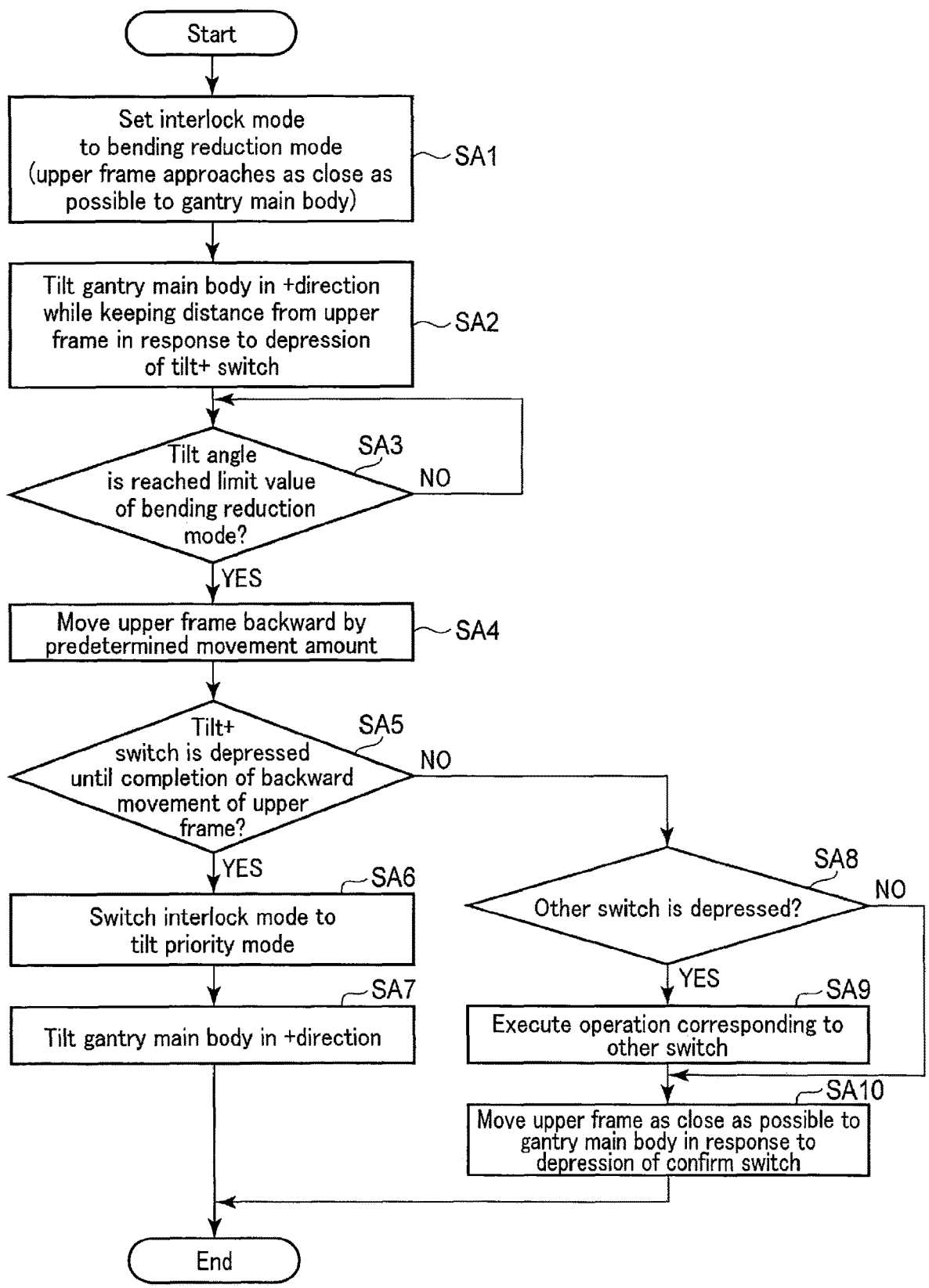
FIG. 8 is a flowchart illustrating the flow of a typical process of the bending reduction mode which is executed under the control of the gantry control circuitry of FIG. 7.
Figure 9:
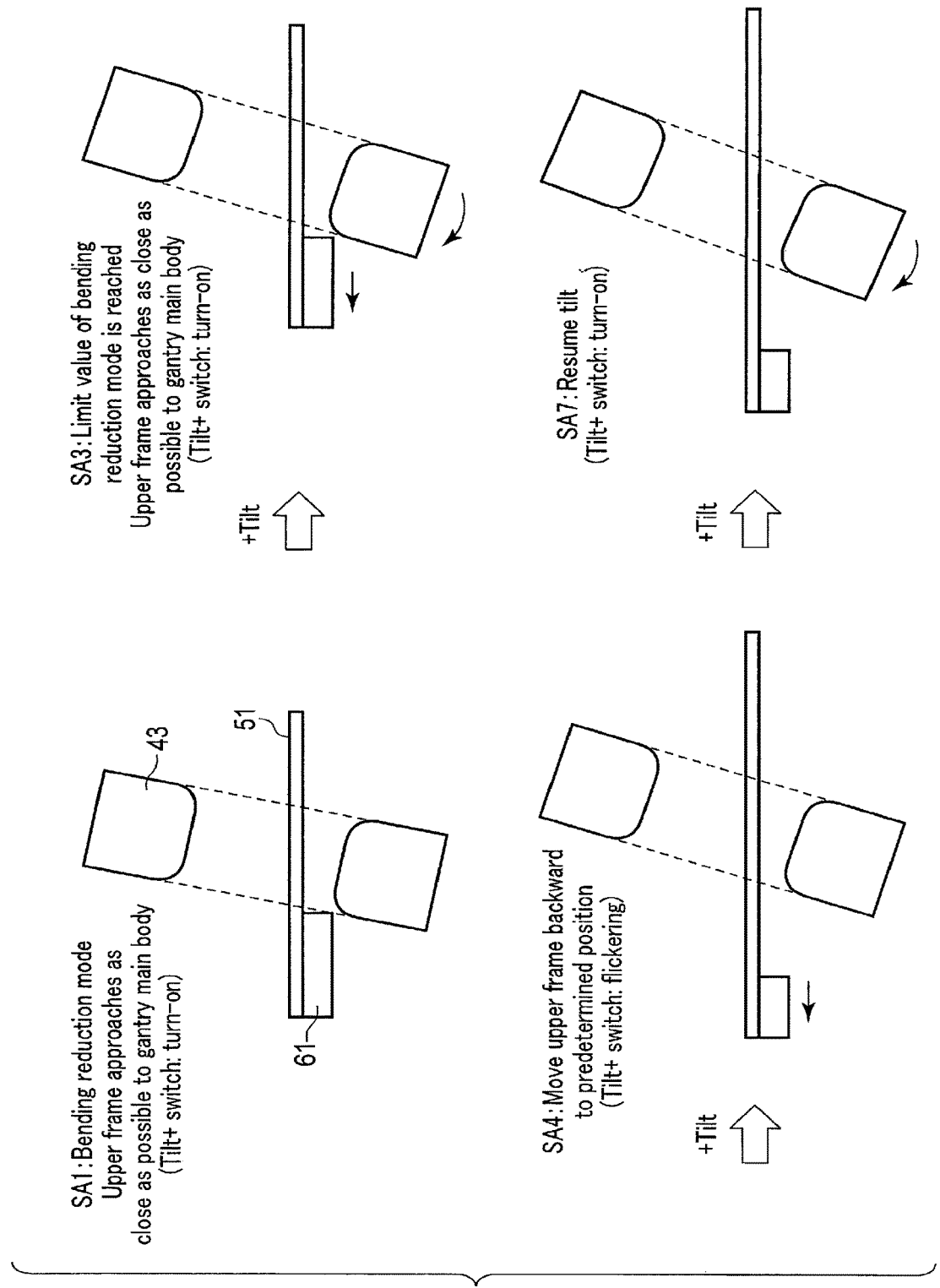
FIG. 9 is a view which schematically illustrates the movement of the gantry main body, table top and upper frame in the flow of the process illustrated in FIG. 8.

Next, the switching of the interlock mode in the bending reduction mode will be described. FIG. 8 is a flowchart illustrating the flow of a typical process of the bending reduction mode which is executed under the control of the gantry control circuitry 35. FIG. 9 is a view which schematically illustrates the movement of the gantry main body 43, table top 51 and upper frame 61 in the flow of the process illustrated in FIG. 8.

As illustrated in FIG. 8, it is first assumed that the tilt angle of the gantry main body 43 is in the angle range RT1 of the bending reduction mode, and that the gantry control circuitry 35 sets the interlock mode to the bending reduction mode by executing the mode switching function 353 (step SA1). In the bending reduction mode, the upper frame 61 is disposed at the proximity distance from the gantry main body 43. Besides, a signal indicating that the interlock mode is the bending reduction mode is supplied from the gantry control circuitry 35 to the light source control circuitry 33.

If the user depresses the tilt+ switch SG1 to instruct a tilt in the +direction, the gantry control circuitry 35 synchronously controls the frame driving control device 64 and tilt driving control device 68, and tilts the gantry main body 43 in the +direction while evacuating the upper frame 61 in the −Z direction (step SA2). In step SA2, the operation timing between the upper frame 61 and gantry main body 43 is not particularly limited. For example, the gantry control circuitry 35 controls the frame driving control device 64 and tilt driving control device 68 in a manner to alternately and intermittently execute the backward movement of the upper frame 61 and the tilt of the gantry main body 43. Alternatively, the gantry control circuitry 35 may control the frame driving control device 64 and tilt driving control device 68 in a manner to move the gantry main body 43 closer to the upper frame 61 to the proximity distance after evacuating the upper frame 61 to a target position. At this time, the frame driving control device 64 and table top driving control device 62 may synchronously be controlled in order to move the table top 51 in the opposite direction (+Z direction) to the movement direction (−Z direction) of the upper frame 61. Thereby, the absolute position of the table top 51 can be kept unchanged, regardless of the movement of the upper frame 61. Thus, the absolute position of the subject P can be fixed before and after the movement of the upper frame 61. While the tilt+ switch is being depressed, the gantry control circuitry 35 operates the upper frame 61 and gantry main body 43.

As illustrated in FIG. 9, while the gantry main body 43 is being tilted, the gantry control circuitry 35 supplies a turn-on signal. The light source control circuitry 33, which has received the turn-on signal, turns on the light source provided on the tilt+ switch SG1. Thereby, the user can be notified that a further tilt operation of the gantry main body 43 is possible.

If step SA2 is executed, the gantry control circuitry 35 judges whether the tilt angle has reached the limit value L1+ of the bending reduction mode (step SA3). Specifically, based on the position signal from the detector 665, the gantry control circuitry 35 measures the height of the upper frame 61, and reads out from the angle range table the angle range RT1 of the bending reduction mode and the angle range RT2 of the tilt priority mode, which correspond to the measured height. In addition, the gantry control circuitry 35 specifies the limit value L1+ of the read-out angle ranges RT. Based on the position signal from the detector 685, the gantry control circuitry 35 measures the tilt angle of the gantry main body 43 in real time, and compares the measured tilt angle with the limit value L1+. Besides, in the bending reduction mode, an electronic or mechanical stopper is set at the limit value L1+. Thereby, a tilt of the gantry main body 43 over the limit value L1+ is electronically or mechanically restricted.

If it is judged in step SA3 that the tilt angle has reached the limit value L1+ of the bending reduction mode (step SA3: YES), the gantry control circuitry 35 controls the frame driving control device 64 and moves the upper frame 61 to a predetermined backward movement position (step SA4). For example, the backward movement position is defined as a Z-directional position of the upper frame 61 where the upper frame 61 does not interfere with the gantry main body 43 even if the tilt angle has reached the limit value L2+ of the tilt priority mode.

As illustrated in FIG. 9, in step SA4, while the upper frame 61 is being moved to the backward movement position, the gantry control circuitry 35 supplies a flicker signal to the light source control circuitry 33. The light source control circuitry 33, which has received the flicker signal, flickers the light source provided on the tilt+ switch SG1. By flickering the light source of the tilt+ switch SG1, the user can be notified that the upper frame 61 moves to the outside of the bending reduction mode. By confirming the tilt+ switch SG1 that is flickering, the user can be aware that the bending of the table top 51 becomes conspicuous in the scan at this tilt angle and the image quality deteriorates accordingly.

While the upper frame 61 is being moved backward, the gantry control circuitry 35 judges whether the tilt+ switch is depressed until the completion of the backward movement of the upper frame 61 to the predetermined backward movement position (step SA5).

If the tilt+ switch is depressed until the upper frame 61 completes the backward movement of the predetermined movement amount (step SA5: YES), the gantry control circuitry 35 controls the interlock circuitry 27 and switches the interlock mode from the bending reduction mode to the tilt priority mode (step SA6). For example, the interlock circuitry 27 electrically or mechanically releases the stopper which is set at the limit value L1+. Thereby, the interlock mode is switched to the tilt priority mode. In the tilt priority mode, an electronical or mechanical stopper is set at the limit value L2+.

If step SA6 is executed, the gantry control circuitry 35 controls the tilt driving control device 68 in response to the depression of the tilt+ switch SG1 by the user, and tilts the gantry main body 43 in the +direction (step SA7). If the user judges that the gantry main body 43 is disposed at a desired tilt angle, the user releases the tilt+ switch SG1. Responding to the release of the tilt+ switch SG1, the gantry control circuitry 35 controls the tilt driving control device 68 and stops the gantry main body 43. Thereafter, using as a trigger the depression of a confirmation switch, for instance, the gantry control circuitry 35 executes an X-ray CT scan.

As illustrated in FIG. 9, while the tilt of the gantry main body 43 is being resumed in step SA7, the gantry control circuitry 35 supplies the turn-on signal to the light source control circuitry 33. The light source control circuitry 33, which has received the turn-on signal, turns on the light source provided on the tilt+ switch SG1.

On the other hand, if the tilt+ switch is not depressed until the upper frame 61 completes the backward movement to the predetermined backward movement position (step SA5: NO), the gantry control circuitry 35 judges whether some other switch was depressed or not (step SA8). This other switch may be any switch if the switch relates to an operation control other than the tilt+ switch SG1. For example, this other switch is the tilt− switch SG2, table top UP switch ST1, table top DOWN switch ST2, table top IN switch ST3, or table top OUT switch ST4.

In step SA8, if some other switch is depressed (step SA8: YES), the gantry control circuitry 35 executes an operation corresponding to the depressed switch (step SA9). For example, if the table top UP switch ST1 is depressed, the gantry control circuitry 35 controls the elevation driving control device 66 and raises the table top 51 while the table top UP button ST1 is being depressed. In step SA9, the positioning of the table top 51 is executed by the operation of the switch other than the tilt+ switch SG1.

In addition, if step SA9 is executed in step SA9 or if the other switch is not depressed in step SA8 (step SA8: NO), the gantry control circuitry 35 controls the frame driving control device 64 in response to the depression of the confirmation switch of the scan, and moves the upper frame 61 as close as possible to the gantry main body 43 (step SA10). Specifically, at a time point of step SA10, since the tilt angle is in the angle range RT1 of the bending reduction mode, the interlock circuitry 27 keeps the bending reduction mode. In this case, the gantry control circuitry 35 moves the upper frame 61 closer to the gantry main body 43 to the proximity distance, based on the depression of the confirmation switch. Thereafter, the gantry control circuitry 35 executes the X-ray CT scan. Accordingly, even when the table top 51 and upper frame 61 were moved by some other switch, the upper frame 61 can automatically be moved as close as possible to the gantry main body 43. Thus, the X-ray CT scan can be executed in the state in which the bending of the table top 51 is small.

By the above, the description of the switching of the interlock mode in the bending reduction mode has been completed.

Figure 10:
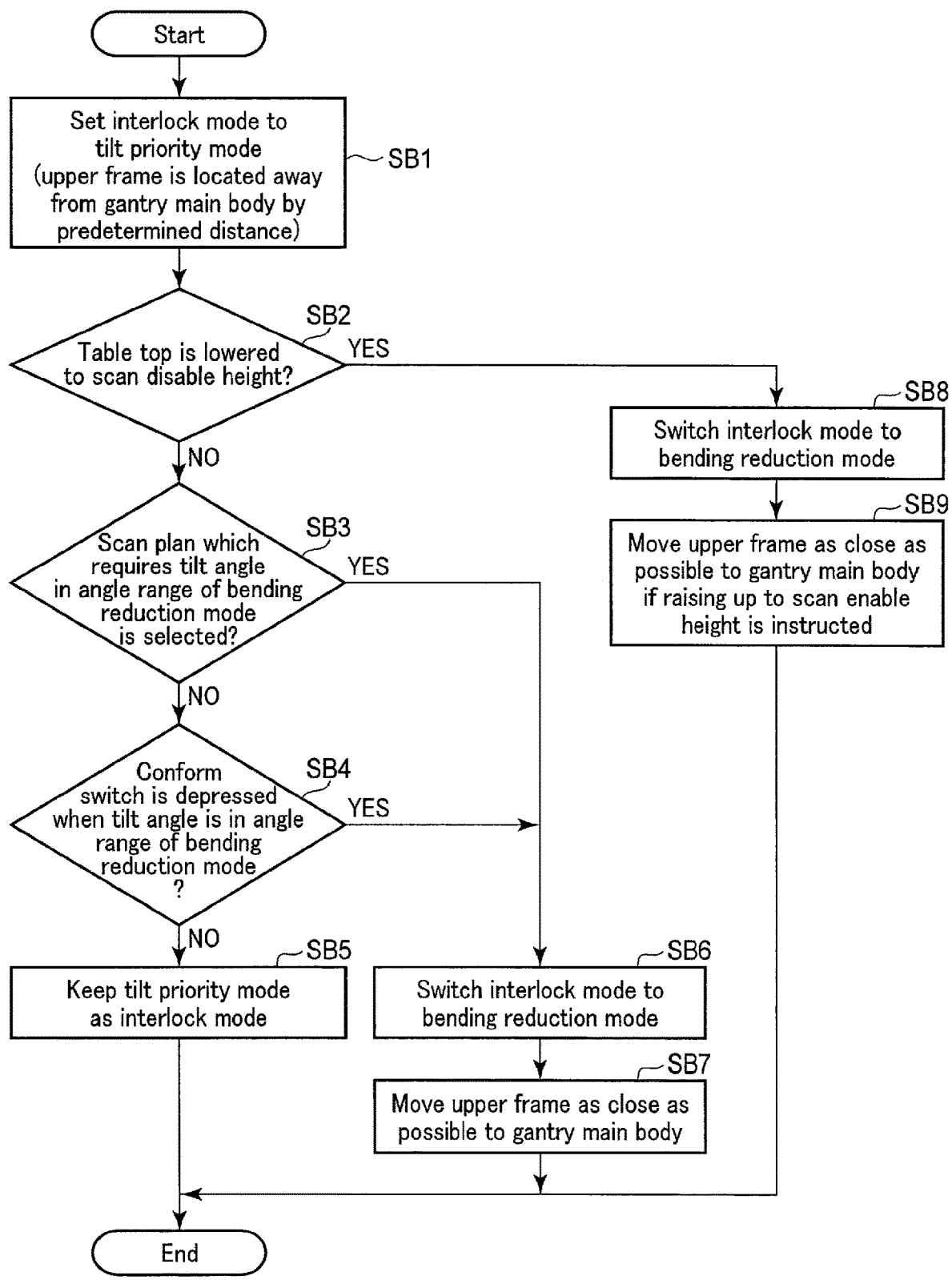
FIG. 10 is a flowchart illustrating the flow of a typical process of a tilt priority mode which is executed under the control of the gantry control circuitry of FIG. 7.

Next, the switching of the interlock mode in the tilt priority mode will be described. FIG. 10 is a flowchart illustrating the flow of a typical process of the tilt priority mode which is executed under the control of the gantry control circuitry 35.

As illustrated in FIG. 10, it is assumed that the tilt angle of the gantry main body 43 is in the angle range RT2 of the tilt priority mode, and that the gantry control circuitry 35 sets the interlock mode to the tilt priority mode by executing the mode switching function 353 (step SB1). In the tilt priority mode, the upper frame 61 is disposed at the proximity distance or more from the gantry main body 43. As this situation, for example, such a case is assumed that the table top 51 is disposed on the outside of the bore 41.

If step SB1 is executed, the gantry control circuitry 35 judges whether the table top 51 is lowered to a scan disable height (step SB2). Concretely, the scan disable height is defined as a height at which the table top 51 cannot be inserted in the bore 41 due to structural restrictions. As the situation in which the table top 51 is not lowered to the scan disable height in the tilt priority mode, it is possible to think of a case in which the subject P, which was carried by a stretcher for the next examination, is moved onto the bed 23. In this case, after an instruction for a change to the next patient was input through the input circuitry 109 or the like, the gantry control circuitry 35 stands by for selection of a new scan plan. Then, the gantry control circuitry 35 executes switching to the interlock mode suitable for the new scan plan that was selected.

If it is judged in step SB2 that the table top 51 is not lowered to the scan disable height (step SB2: NO), the gantry control circuitry 35 judges whether a scan plan, which requires a tilt angle in the angle range RT1 of the bending reduction mode, was selected or not (step SB3). The scan plan which requires the tilt angle in the angle range RT1 of the bending reduction mode is, in other words, a scan plan which does not require a tilt angle in the angle range RT2 of the tilt priority mode. For example, the tilt angle relating to the scan of the lumbar part or head part needs to be a relatively large tilt angle. In this case, the interlock mode may be set to the tilt priority mode. Conversely, for example, a tilt angle relating to the scan which requires deep insertion of the table top 51, such as helical scan in which the table top 51 is moved while the rotary frame 11 is being rotated, or shuttle helical scan in which the table top 51 is reciprocally moved while the rotary frame 11 is being rotated, needs to be a relatively small tilt angle. In this case, the interlock mode may be set to the bending reduction mode. In this manner, the gantry control circuitry 35 can set the interlock mode to the bending reduction mode or to the tilt priority mode as a default in accordance with the selected scan plan.

In step SB3, the gantry control circuitry 35 judges whether the tilt angle in the selected scan plan is included in the angle range RT1 corresponding to an estimated height of the table top 51. If the tilt angle in the selected scan plan is included in the angle range RT1, the gantry control circuitry 35 judges that the scan plan which requires the tilt angle in the angle range RT1 is selected. If the tilt angle in the selected scan plan is not included in the angle range RT1, the gantry control circuitry 35 judges that the scan plan which requires the tilt angle in the angle range RT1 is not selected.

If it is judged in step SB3 that the scan plan which requires the tilt angle in the angle range RT1 is not selected (step SB3: NO), the gantry control circuitry 35 judges whether the confirmation switch of the scan was depressed when the tilt angle is in the angle range RT1 (step SB4). As another situation in which the table top 51 is not lowered to the scan disable height in the tilt priority mode, it is possible to think of, for example, a case in which the table top 51 is once moved backward out of the bore 41 during the examination. In this case, the gantry control circuitry 35 stands by for selection of a new scan plan for the same subject P. Then, the gantry control circuitry 35 executes switching to the interlock mode suitable for the new selected scan plan.

If it is judged in step SB4 that the confirmation switch is not depressed when the tilt angle is in the angle range RT1 of the bending reduction mode (step SB4: NO), the gantry control circuitry 35 keeps the tilt priority mode as the interlock mode (step SB5). In this case, since an X-ray CT scan in the bending reduction mode is not assumed, the tilt priority mode is maintained.

On the other hand, if it is judged in step SB3 that the scan plan which requires the tilt angle in the angle range of the bending reduction mode is selected (step SB3: YES) or if it is judged in step SB4 that the confirmation switch was depressed when the tilt angle is in the angle range of the bending reduction mode (step SB4: YES), the gantry control circuitry 35 switches the interlock mode to the bending reduction mode (step SB6).

If step SB6 is executed, the gantry control circuitry 35 controls the frame driving control device 64 and moves the upper frame 61 as close as possible to the gantry main body 43 (step SB7). Thereafter, the gantry control circuitry 35 executes the X-ray CT scan in the bending reduction mode.

On the other hand, if it is judged in step SB2 that the table top 51 is lowered to the scan disable height (step SB2: YES), the gantry control circuitry 35 switches the interlock mode to the bending reduction mode (step SB8). As the situation in step SB8, it is assumed that the subject is moved off from the table top 51 at the scan disable height and the subject is changed for the next examination. Thus, the interlock mode may be set to the bending reduction mode that is the default. In the meantime, when an instruction to lower the table top 51 from a scan enable height to the scan disable height was input, the gantry control circuitry 35 controls the table top driving control device 62 to move the table top 51 backward to the outside of the bore 41, and controls the tilt driving control device 68 to restore the tilt angle of the gantry main body 43 to 0°. Then, the gantry control circuitry 35 controls the elevation driving control device 66 to lower the table top 51 to the scan disable height. Accordingly, in step SB8, the tilt angle of the gantry main body 43 is set at 0°.

If step SB8 is executed, the gantry control circuitry 35 controls the frame driving control device 64 and moves the upper frame 61 as close as possible to the gantry main body 43 (step SB9). Specifically, the gantry control circuitry 35 first raises the table top 51 to the scan enable height in response to the depression of the table top UP switch ST1, for instance. The scan enable height is defined as such a height that the table top 51 can be inserted into the bore 41. After raising the table top 51 to the scan enable height, the gantry control circuitry 35 controls the table top driving control device 62 and tilt driving control device 68, thereby positioning the table top 51 and gantry main body 43. Further, the gantry control circuitry 35 controls the frame driving control device 64, thereby moving the upper frame 61 as close as possible to the gantry main body 43. Thereafter, the gantry control circuitry 35 executes the X-ray CT scan in the bending reduction mode.

By the above, the description of the switching of the interlock mode in the tilt priority mode has been completed.

Besides, the flow of the process in the tilt priority mode is not limited to the flow illustrated in FIG. 10, and various modifications are possible. For example, in step SBB, like step SB5 or SB6, the gantry control circuitry 35 may set the interlock mode corresponding to the scan plan. In addition, the order of step SB3 and step SB4 may be reversed.

As described above, the X-ray computed tomography apparatus according to the present embodiment includes the gantry 10, bed 23 and gantry control circuitry 35. The gantry 10 includes the gantry main body 43 and base 45. The gantry main body 43 is equipped with the X-ray tube 13 and X-ray detector 15. The base 45 tiltably supports the gantry main body 43. The bed 23 includes the upper frame 61 and lower frame 63. The upper frame 61 supports the table top 51 on which the subject is placed, such that the table top 51 is movable in the longitudinal direction. The lower frame 63 supports the upper frame 61 such that the upper frame 61 is movable in the longitudinal direction. The gantry control circuitry 35 includes the movement control function 355 and mode switching function 353. In the movement control function 355, the gantry control circuitry 35 controls the tilt of the gantry main body 43, the movement of the table top 51 by the upper frame 61, and the movement of the upper frame 61 by the lower frame 63. In the mode switching function 353, the gantry control circuitry 35 executes switching between the bending reduction mode in which the gantry main body 43 is tilted in a first angle range RT1, and the tilt priority mode in which the gantry main body 43 is tilted in a second angle range RT2 in which the tilt angle is greater than in the first angle range RT1.

According to the above configuration, the X-ray computed tomography apparatus of the present embodiment can execute switching between the bending reduction mode and tilt priority mode. Typically, the X-ray computed tomography apparatus according to this embodiment can execute switching between the bending reduction mode and tilt priority mode in accordance with the tilt angle. Thus, at the time of positioning, the user can pay attention to only the tilt angle without being aware of the upper frame 61. Thereby, the bending of the table top 51 can be reduced while the same operability as in the conventional X-ray computed tomography apparatus having no bending reduction mode is maintained.

In the above embodiment, the switching of the interlock mode at the time of tilting was described, but the embodiment is not restricted to this.

(Modification 1)

Gantry control circuitry 35 according to Modification 1 switches the interlock mode when the table top 51 moves in a transverse direction. Modification 1 will be described below. In the description below, the structural elements having substantially the same functions as in the present embodiment are denoted by like reference numerals, and an overlapping description will be given only where necessary.

The lower frame 63 of the bed 23 according to Modification 1 supports the table top 51 and upper frame 61 such that the table top 51 and upper frame 61 are also slidable in a direction parallel to the transverse axis of the table top 51, that is, in the X direction (transverse direction). The gantry/bed driving system 25 includes a transverse-axis slide driving control device (not shown) for sliding (i.e. right-and-left movement) in the X direction. The gantry control circuitry 35 controls the transverse-axis slide driving control device of the gantry/bed driving system 25, and slides the table top 51 and upper frame 61 as one body in the X direction. The interlock circuitry 27 switches the interlock mode relating to the right-and-left movement of the table top 51 and upper frame 61 between a first right-and-left movement mode and a second right-and-left movement mode. The first right-and-left movement mode is an interlock mode in which the upper frame 61 is moved as close as possible to the gantry main body 43 in order to reduce the bending of the table top 51. The second right-and-left movement mode is an interlock mode in which priority is placed on the right-and-left movement of the table top 51 over the reduction of bending.

Like the case of the time of tilting, the gantry control circuitry 35 according to Modification 1 executes the position measuring function 351, mode switching function 353 and movement control function 355. In the mode switching function 353, the gantry control circuitry 35 controls the interlock circuitry 27 in accordance with the position between the gantry main body 43 and upper frame 61, and executes switching between the first right-and-left movement mode in which the table top 51 is moved in the right-and-left direction in a first movement range and the second right-and-left movement mode in which the table top 51 is moved in the right-and-left direction in a second movement range which is outside of the first right-and-left movement range in the X direction. For example, the first movement range in the case in which the table top 51 or upper frame 61 is at a predetermined height is defined as a range of −30 cm to +30 cm in the X direction with the isocenter being set at 0 cm. The second movement range is defined as a range of −45 cm to −30 cm in the X direction and as a range of +30 cm to +45 cm in the X direction. Because of the structures of the gantry 10 and bed 23, the first movement range and second movement range vary in accordance with the height of the upper frame 61. The gantry control circuitry 35 switches the interlock mode between the first right-and-left movement mode and the second right-and-left movement mode in accordance with the height and X-directional position of the upper frame 61.

As described above, also at the time of the right-and-left movement of the table top 51, the X-ray computed tomography apparatus according to Modification 1 can reduce the bending of the table top 51 while maintaining the same operability as in the conventional X-ray computed tomography apparatus, without the user being aware of the upper frame 61.

(Modification 2)

Gantry control circuitry 35 according to Modification 2 switches the interlock mode when the gantry main body 43 is slewed. Modification 2 will be described below. In the description below, the structural elements having substantially the same functions as in the present embodiment are denoted by like reference numerals, and an overlapping description will be given only where necessary.

The gantry/bed driving system 25 according to Modification 2 slews the gantry main body 43 about a slew axis. The slew axis is a vertical axis parallel to the Y axis. The slew axis is set to penetrate a substantially middle portion of the gantry main body 43 along the X axis. The gantry/bed driving system 25 includes a slew driving control device (not shown) for slewing. The gantry control circuitry 35 controls the slew driving control device of the gantry/bed driving system 25, thereby slewing the gantry main body 43 about the slew axis. The interlock circuitry 27 switches the interlock mode relating to the slew of the gantry main body 43 between a first slew mode and a second slew mode. The first slew mode is an interlock mode in which the upper frame 61 is moved as close as possible to the gantry main body 43 in order to reduce the bending of the table top 51. The second slew mode is an interlock mode in which priority is placed on the slew of the gantry main body 43 over the reduction of bending.

Like the case of the time of tilting, the gantry control circuitry 35 according to Modification 2 executes the position measuring function 351, mode switching function 353 and movement control function 355. In the mode switching function 353, the gantry control circuitry 35 controls the interlock circuitry 27 in accordance with the position between the gantry main body 43 and upper frame 61, and executes switching between the first slew mode in which the gantry main body 43 is slewed in a first slew angle range and the second slew mode in which the gantry main body 43 is slewed in a second slew angle range in which the slew angle is greater than in the first slew angle range. For example, the first slew angle range in the case in which the table top 51 or upper frame 61 is at a predetermined height is defined as a range of −10° to +10° when the slew angle about the slew axis at a time when the gantry main body 43 is parallel to the X-axis direction is set at 0°. The second slew angle range is defined as a range of −15° to −10° and as a range of +10° to +15°. Because of the structures of the gantry 10 and bed 23, the first slew angle range and second slew angle range vary in accordance with the height of the upper frame 61. The gantry control circuitry 35 switches the interlock mode between the first slew mode and the second slew mode in accordance with the height of the upper frame 61 and the slew angle of the gantry main body 43.

As described above, also at the time of the slewing of the gantry main body 43, the X-ray computed tomography apparatus according to Modification 2 can reduce the bending of the table top 51 while maintaining the same operability as in the conventional X-ray computed tomography apparatus, without the user being aware of the upper frame 61.

According to at least one of the above-described embodiments, while the bending of the table top is reduced, the gantry and bed can easily be positioned.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
 a gantry main body equipped with an X-ray tube and an X-ray detector;
 a base configured to tiltably support the gantry main body;
 a first support frame configured to support a table top, on which a subject is placed, such that the table top is movable in a longitudinal direction;
 a second support frame configured to support the first support frame such that the first support frame is movable in the longitudinal direction; and
 gantry control circuitry configured to control a tilt of the gantry main body, a movement of the table top by the first support frame, and a movement of the first support frame by the second support frame, and configured to execute switching between a first tilt mode in which the gantry main body is tiltable in a first angle range and a second tilt mode in which the gantry main body is tiltable in a second angle range in which a tilt angle is greater than in the first angle range.

2. The X-ray computed tomography apparatus of claim 1, wherein when the gantry control circuitry switches the first tilt mode to the second tilt mode, the gantry control circuitry is configured to control the second support frame such that the first support frame moves in a direction in which the first support frame moves away from the gantry main body.

3. The X-ray computed tomography apparatus of claim 1, wherein the gantry control circuitry is configured to switch the first tilt mode to the second tilt mode in accordance with the tilt angle of the gantry main body and a height of the table top or the first support frame.

4. The X-ray computed tomography apparatus of claim 1, further comprising:
 a first switch configured to instruct a tilt in a first direction in which a lower portion of the gantry main body moves toward the first support frame; and
 a tilt angle detector configured to detect the tilt angle of the gantry main body,
 wherein the gantry control circuitry is configured to tilt the gantry main body in the first direction when the tilt in the first direction is instructed by the first switch in the first tilt mode, and configured to stop the tilt of the gantry main body when the detected tilt angle has reached a predetermined angle.

5. The X-ray computed tomography apparatus of claim 4, wherein when the instruction for the tilt by the first switch ends before the detected tilt angle reaches the predetermined angle, the gantry control circuitry is configured to move the first support frame in a second direction which is opposite to the first direction, and to move the first support frame closer to the gantry main body to a predetermined distance.

6. The X-ray computed tomography apparatus of claim 4, further comprising light source control circuitry configured to control a light source provided in the first switch,
 wherein the light source control circuitry is configured to turn on the light source when the detected tilt angle does not reach the predetermined angle, and configured to flicker the light source when the detected tilt angle has reached the predetermined angle.

7. The X-ray computed tomography apparatus of claim 4, wherein the gantry control circuitry is configured to switch the first tilt mode to the second tilt mode if a further tilt in the first direction is instructed by the first switch at a time when the tilt of the gantry main body in the first direction is stopped.

8. The X-ray computed tomography apparatus of claim 4, further comprising light source control circuitry configured to control a light source provided in the first switch,
 wherein the light source control circuitry is configured to flicker the light source while the first support frame is being moved backward, configured to further tilt the gantry main body in the first direction after the first support frame is moved backward, and configured to turn on the light source while the gantry main body is being tilted in the first direction.

9. The X-ray computed tomography apparatus of claim 4, further comprising a second switch configured to instruct an operation other than the tilt in the first direction in which the lower portion of the gantry main body moves toward the first support frame,
 wherein the gantry control circuitry is configured to execute the other operation if the other operation is instructed by the second switch at a time when the tilt of the gantry main body in the first direction is stopped.

10. The X-ray computed tomography apparatus of claim 9, wherein the gantry control circuitry is configured to move the first support frame closer to the gantry main body to a predetermined distance in the first angle range, if the other operation is finished or if the other operation is not instructed by the second switch at a time when the tilt of the gantry main body in the first direction is stopped.

11. The X-ray computed tomography apparatus of claim 1, further comprising a third support frame configured to vertically movably support the first support frame and the second support frame,
wherein the gantry control circuitry is configured to switch the second tilt mode to the first tilt mode when the table top has lowered to a scan disable height in the second tilt mode.

12. The X-ray computed tomography apparatus of claim 11, wherein after the switching to the first tilt mode, the gantry control circuitry is configured to move the first support frame closer to the gantry main body to a predetermined distance in the first angle range.

13. The X-ray computed tomography apparatus of claim 11, wherein if lowering of the table top from a scan enable height to the scan disable height is instructed, the gantry control circuitry is configured to tilt the gantry main body to a tilt angle of 0° and then to lower the table top to the scan disable height.

14. The X-ray computed tomography apparatus of claim 11, further comprising processing circuitry configured to select a scan plan,
wherein the gantry control circuitry is configured to switch the second tilt mode to the first tilt mode if the table top lowers to the scan disable height in the second tilt mode and if the selected scan plan requires a tilt angle in the first angle range.

15. The X-ray computed tomography apparatus of claim 11, further comprising an execution switch configured to instruct execution of a scan,
wherein the gantry control circuitry is configured to switch the second tilt mode to the first tilt mode when the execution of the scan is instructed by the execution switch in a case in which the table top lowers to the scan disable height in the second tilt mode and the tilt angle of the gantry main body is in the first angle range.

16. The X-ray computed tomography apparatus of claim 1, further comprising processing circuitry configured to select a scan plan,
wherein the gantry control circuitry is configured to set one of the first tilt mode and the second tilt mode in accordance with the selected scan plan.

17. The X-ray computed tomography apparatus of claim 16, wherein the gantry control circuitry is configured to set the first tilt mode if the selected scan plan requires a tilt angle in the first angle range, and configured to set the second tilt mode if the selected scan plan requires a tilt angle in the second angle range.

18. The X-ray computed tomography apparatus of claim 1, wherein the gantry control circuitry is configured to alternately execute in the first tilt mode the movement of the first support frame and the tilt of the gantry main body.

19. An X-ray computed tomography apparatus comprising:
a gantry main body equipped with an X-ray tube and an X-ray detector;
a first support frame configured to support a table top, on which a subject is placed, such that the table top is movable in a longitudinal direction;
a second support frame configured to support the first support frame such that the first support frame is movable in a transverse direction; and
gantry control circuitry configured to control a tilt of the gantry main body, a movement of the table top by the first support frame, and a movement of the first support frame by the second support frame, and configured to execute switching between a first movement mode in which the first support frame is movable in a first movement range in the transverse direction and a second movement mode in which the first support frame is movable in a second movement range which is outside the first movement range in the transverse direction.

20. An X-ray computed tomography apparatus comprising:
a gantry main body equipped with an X-ray tube and an X-ray detector;
a base configured to support the gantry main body such that the gantry main body is slewable about a vertical axis;
a first support frame configured to support a table top, on which a subject is placed, such that the table top is movable in a longitudinal direction;
a second support frame configured to support the first support frame such that the first support frame is movable in the longitudinal direction; and
gantry control circuitry configured to control a tilt of the gantry main body, a movement of the table top by the first support frame, and a movement of the first support frame by the second support frame, and configured to execute switching between a first slew mode in which the gantry main body is slewable in a first slew angle range and a second slew mode in which the gantry main body is slewable in a second slew angle range in which a slew angle is greater than in the first slew angle range.

* * * * *